United States Patent
Soma et al.

(10) Patent No.: US 10,475,470 B2
(45) Date of Patent: Nov. 12, 2019

(54) PROCESSING RESULT ERROR DETECTION DEVICE, PROCESSING RESULT ERROR DETECTION PROGRAM, PROCESSING RESULT ERROR DETECTION METHOD, AND MOVING ENTITY

(71) Applicant: HONDA MOTOR CO., LTD., Tokyo (JP)

(72) Inventors: Eisuke Soma, Wako (JP); Hiromitsu Yuhara, Wako (JP); Tomoko Shintani, Wako (JP); Shinichiro Goto, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 15/720,152

(22) Filed: Sep. 29, 2017

(65) Prior Publication Data

US 2018/0096698 A1   Apr. 5, 2018

(30) Foreign Application Priority Data

Sep. 30, 2016 (JP) .................. 2016-195193

(51) Int. Cl.

| | |
|---|---|
| *G06F 15/16* | (2006.01) |
| *G06F 15/173* | (2006.01) |
| *G10L 25/63* | (2013.01) |
| *A61B 5/18* | (2006.01) |
| *B60K 28/06* | (2006.01) |

(Continued)

(52) U.S. Cl.
CPC .............. *G10L 25/63* (2013.01); *A61B 5/165* (2013.01); *A61B 5/18* (2013.01); *A61B 5/7264* (2013.01); *A61B 5/7267* (2013.01); *B60K 28/06* (2013.01); *G08B 21/02* (2013.01)

(58) Field of Classification Search
USPC .................................... 704/9; 709/203, 219
See application file for complete search history.

(56) References Cited

U.S. PATENT DOCUMENTS

| | | | | |
|---|---|---|---|---|
| 5,029,214 A | * | 7/1991 | Hollander | ................ A63H 3/28 446/175 |
| 9,245,176 B2 | * | 1/2016 | Matthews | ............... G06T 13/40 |

(Continued)

FOREIGN PATENT DOCUMENTS

| | | |
|---|---|---|
| JP | 2000-259178 A | 9/2000 |
| JP | 2002-182680 A | 6/2002 |

(Continued)

OTHER PUBLICATIONS

Office Action dated Jul. 9, 2019, issued in counterpart JP application No. 2016-195193, with English translation. (6 pages).

*Primary Examiner* — Seong-Ah A Shin
(74) *Attorney, Agent, or Firm* — Westerman, Hattori, Daniels & Adrian, LLP

(57) ABSTRACT

A processing result error detection device includes: a behavior recognition unit which recognizes behavior of a user; a processing unit which executes a process dependent on the behavior of the user; an emotion presumption unit which presumes an intensity of emotion of the user based on reaction of the user to a processing result; and a judgment unit which judges that the processing result includes an error when the presumed intensity of emotion of the user is equal to or greater than a predetermined threshold.

11 Claims, 6 Drawing Sheets

(51) Int. Cl.
  *G08B 21/02* (2006.01)
  *A61B 5/00* (2006.01)
  *A61B 5/16* (2006.01)

(56) References Cited

U.S. PATENT DOCUMENTS

| | | | | |
|---|---|---|---|---|
| 2006/0122834 A1* | 6/2006 | Bennett | ............... | G10L 15/1822 704/256 |
| 2008/0269958 A1* | 10/2008 | Filev | ................ | B60W 50/10 701/1 |
| 2011/0083075 A1* | 4/2011 | MacNeille | ............ | B60K 37/06 715/728 |
| 2012/0089705 A1* | 4/2012 | French | ................. | G06Q 30/01 709/219 |
| 2013/0116856 A1* | 5/2013 | Schadeck | .............. | B60K 28/06 701/1 |
| 2013/0144937 A1* | 6/2013 | Lee | ........................ | G06N 7/023 709/203 |
| 2014/0191872 A1* | 7/2014 | Gomi | ................ | G06Q 30/0201 340/573.1 |
| 2015/0053066 A1* | 2/2015 | Hampiholi | ............ | B60W 50/14 84/602 |
| 2015/0213331 A1* | 7/2015 | Peng | .................. | G06K 9/00684 382/165 |
| 2016/0026237 A1* | 1/2016 | Moriguchi | ................ | G06F 3/01 345/156 |
| 2018/0032610 A1* | 2/2018 | Cameron | ................ | G10L 15/18 |

FOREIGN PATENT DOCUMENTS

| | | |
|---|---|---|
| JP | 2002-221429 A | 8/2002 |
| JP | 2009-210992 A | 9/2009 |
| JP | 2010-128015 A | 6/2010 |
| JP | 2013-216241 A | 1/2013 |
| JP | 2016-149063 A | 8/2016 |

* cited by examiner

PROCESSING RESULT ERROR DETECTION DEVICE, PROCESSING RESULT ERROR DETECTION PROGRAM, PROCESSING RESULT ERROR DETECTION METHOD, AND MOVING ENTITY

CROSS REFERENCES TO RELATED APPLICATIONS

The present application claims priority under 35 U.S.C. § 119 to Japanese Patent Application No. 2016-195193, filed Sep. 30, 2016, entitled "Processing Result Error Detection Device, Processing Result Error Detection Program, Processing Result Error Detection Method, and Moving Entity." The contents of this application are incorporated herein by reference in their entirety.

TECHNICAL FIELD

The present disclosure relates to a processing result error detection device, a processing result error detection program, a processing result error detection method, and a moving entity.

BACKGROUND

There is a conventionally known vehicle-mounted device for providing road navigation which analyzes the voice of a user caught on a microphone, and recognizes the instruction of the user in the form of voice (see Japanese Unexamined Patent Application Publication No. 2002-221429).

For example, Japanese Unexamined Patent Application Publication No. 2002-221429 proposes a technique in which: when a driver as a user gives an instruction to provide road navigation, a judgment is made as to whether or not the driver is in a calm state; if the judgment result is negative, a judgment is made as to how much the driver is in a hurry; and the type of voice for the road navigation is switched based on the judged degree of hurry.

Also, Japanese Unexamined Patent Application Publication No. 2000-259178 discloses a technique of reporting a recognition error.

However, the inputted voice of a user may fail to be recognized correctly because of, for example, ambient noise or a pronunciation peculiar to the user. In such a case, an erroneous event is, for instance, uploaded via a communication network to an external management center for the purpose of providing feedback to the system or application. Some events are difficult to determine as errors, but some events can be clearly recognized as voice recognition errors. However, it is bothersome for the user to perform work such as uploading all erroneous events one by one suspecting that they are errors. In addition, if the user is requested to distinguish the types of errors, the user may be annoyed with the work.

SUMMARY

In view of the above, it is preferable to provide a processing result error detection device, a processing result error detection program, a processing result error detection method, and a moving entity which are capable of detecting a processing result error while reducing or solving bother given to the user.

A processing result error detection device of one aspect of the present disclosure includes: a behavior recognition unit which recognizes behavior of a user including reaction of the user; a processing unit which executes a process dependent on the behavior of the user; an emotion presumption unit which presumes an intensity of emotion of the user based on the reaction of the user to a processing result being a result of the process; and a judgment unit which judges the processing result as erroneous if the presumed intensity of emotion of the user is equal to or greater than a predetermined threshold.

In the processing result error detection device of the present disclosure, it is preferable that the emotion presumption unit be configured to presume a type of emotion of the user as well as the intensity of emotion of the user based on the reaction of the user to the processing result, and the judgment unit set the threshold to a smaller value compared to a case where the type of emotion of the user is a positive type if the type of emotion of the user is a negative type.

In the processing result error detection device of the present disclosure, it is preferable that the judgment unit judge the processing result as a first error with erroneous recognition of an instruction of the user if the intensity of emotion of the user is equal to or greater than a predetermined first threshold, and judge the processing result as a second error without the erroneous recognition of the instruction of the user if the intensity of emotion of the user is less than the first threshold and is equal to or greater than a second threshold smaller than the first threshold.

In the processing result error detection device of the present disclosure, it is preferable that the emotion presumption unit presume the intensity of emotion of the user before the process based on the behavior of the user corresponding to the instruction of the user, and the judgment unit determine the threshold based on the intensity of emotion of the user before the process.

In the processing result error detection device of the present disclosure, it is preferable that the emotion presumption unit be configured to presume the type of emotion of the user as well as the intensity of emotion of the user based on the reaction of the user to the processing result, and the judgment unit judge the processing result as erroneous if the type of emotion of the user is a specific type and the intensity of emotion of the user is equal to or greater than the threshold.

In the processing result error detection device of this configuration, it is preferable that the specific type include a positive type of emotion.

According to one embodiment of a processing result error detection device, a processing result error detection program, a processing result error detection method, and a moving entity of the present disclosure, it is possible to judge an erroneous processing result while reducing or solving bother given to the user.

BRIEF DESCRIPTION OF THE DRAWINGS

The advantages of the disclosure will become apparent in the following description taken in conjunction with the following drawings.

DETAILED DESCRIPTION

With reference to FIGS. 1 to 7D, description is provided for one embodiment of a processing result error detection device, a processing result error detection program, a processing result error detection method, and a moving entity (or a mobile unit) of the present disclosure.

Figure 1:
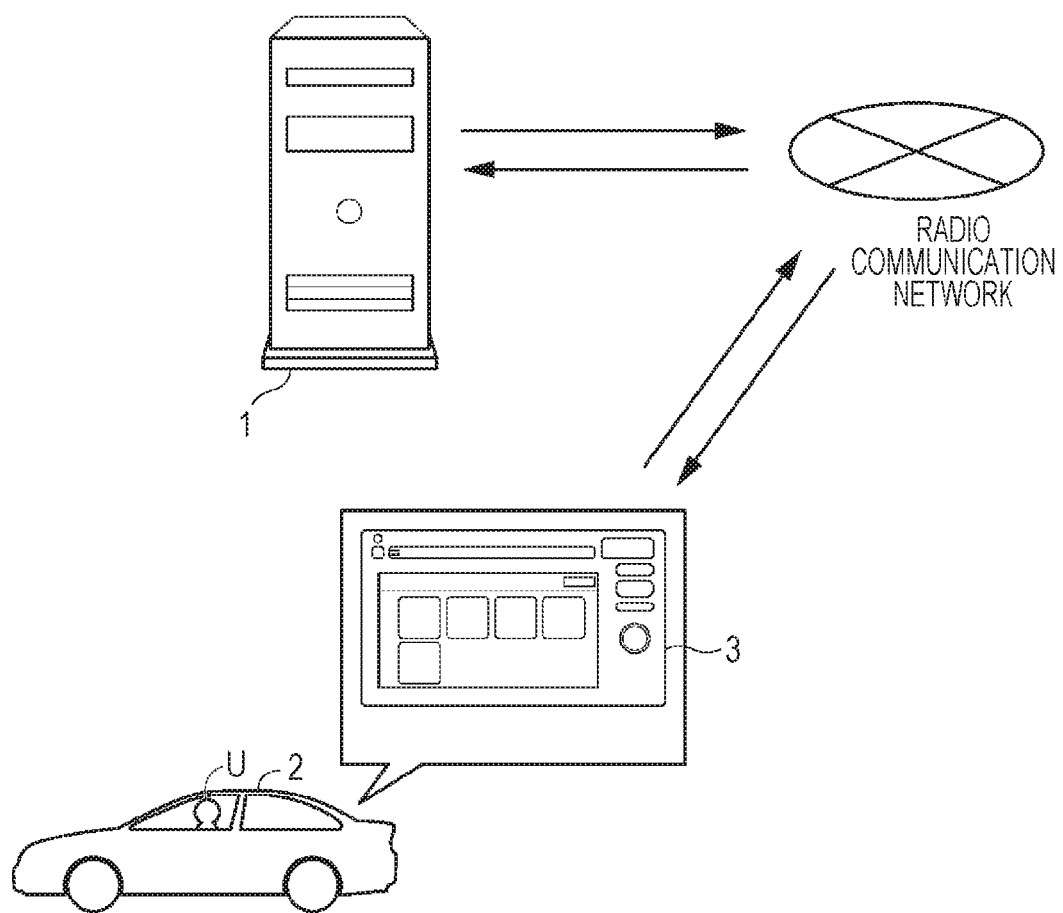
FIG. 1 is an overall configuration diagram of a processing result error detection system of an embodiment.

As illustrated in FIG. 1, a processing result error detection system includes: a server 1; a plurality of moving entities 2; and an agent device 3 (processing result error detection device) mounted on each of the moving entities 2. The server 1 and the agent device 3 are communicably connected to each other via a radio (or wireless) communication network. The moving entity 2 is a vehicle, for example, and its occupant is referred to as a user U in this specification. Although FIG. 1 illustrates a situation where there is one occupant (user U) on board in one moving entity, more than one occupant may be on board in one moving entity.

(Server Configuration)

The server 1 includes one or more computers. The server 1 is configured to receive data and a request from each agent device 3, store the data in a storage unit such as a database, execute processes in accordance with the request, and transmit a processing result to the agent device 3.

Some or all of the computers constituting the server 1 may include mobile stations, for example one or more constituents of the agent device 3.

That the constituents of the present disclosure are "configured" to execute assigned arithmetic processes means that arithmetic processing units such as CPUs constituting those constituents are "programmed" or "designed" to read software in addition to necessary information from a recording media or a memory such as a ROM or a RAM, and to execute an arithmetic process on that information in accordance with the software. The constituents may share a common processor (arithmetic processing unit). Alternatively, each of the constituents may include a plurality of processors capable of communicating with one another.

(Configuration of Moving Entity)

The moving entity 2 is, for example, a four-wheel automobile. In addition to the above or alternatively, the moving entity 2 may be a two-wheel automobile, a bicycle, a robot, or an inverted pendulum vehicle, for example.

Figure 2:
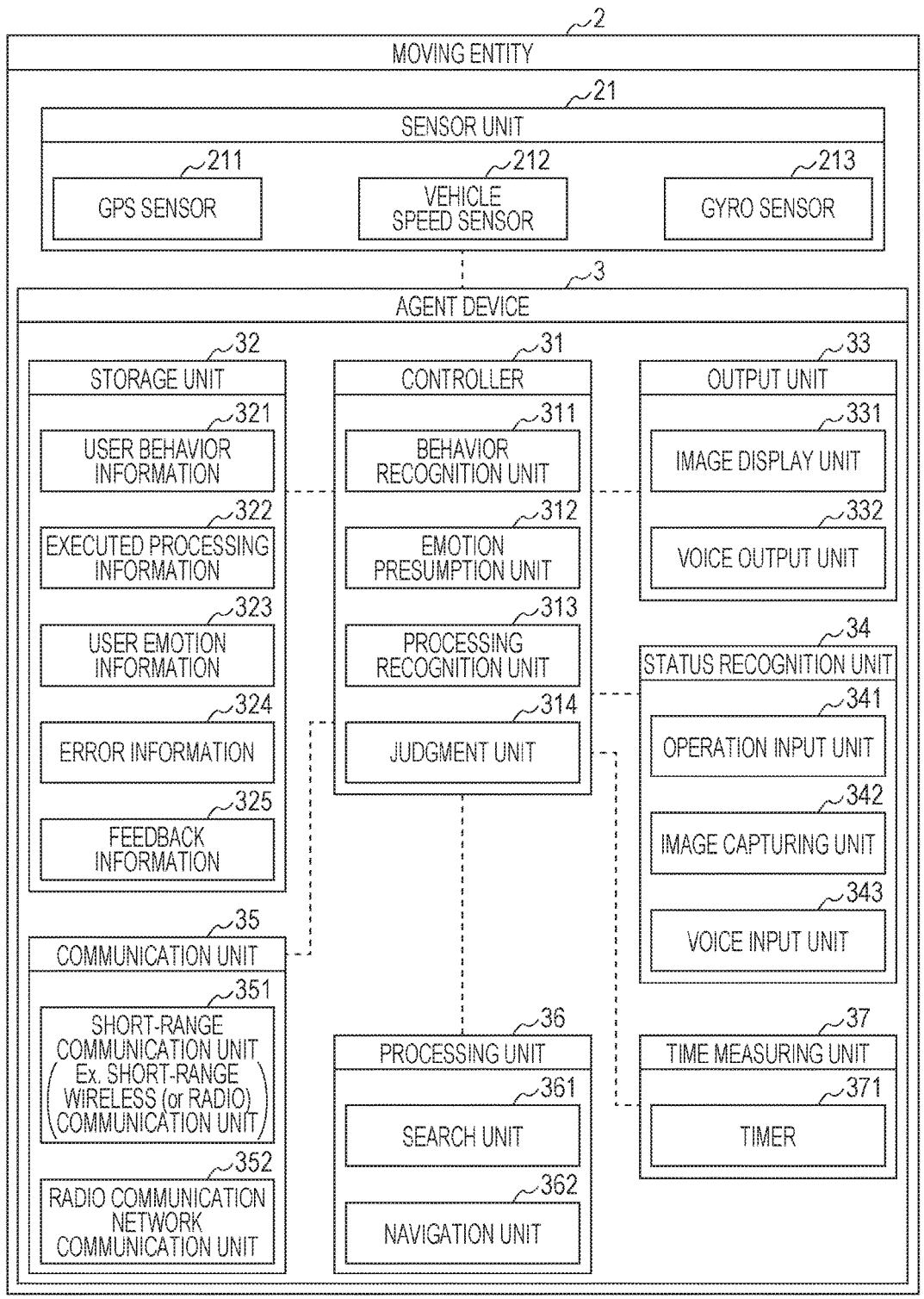
FIG. 2 is a block diagram of an agent device.

As illustrated in FIG. 2, the moving entity 2 includes: a sensor unit 21 which outputs signals indicating statuses of the moving entities 2; and the agent device 3 which is connected to the sensor unit 21 by wireless connection or cable connection.

The sensor unit 21 includes: a GPS sensor 211 which acquires the current location of the moving entity 2; a vehicle speed sensor 212 which acquires the moving speed of the moving entity 2; and a gyro sensor 213 which acquires the angular speed of the moving entity 2. The sensor unit 21 is configured to also acquire, with use of a not—illustrated sensor, the status of an ignition switch of the moving entity 2, the instructed amount of operation on the moving entity 2 such as acceleration or braking, and information on instruments equipped on the other moving entities 2. The sensor unit 21 is configured to output the acquired information to the agent device 3.

(Configuration of Agent Device)

The agent device 3 is an information terminal such as a navigation device whose size or the like is designed such that the agent device 3 can be mounted on the moving entity 2 in which the user U (occupant of the moving entity) is on board.

The agent device 3 may be an information terminal whose size, shape, and weight are designed such that the user U can carry with, such as a tablet terminal or a radio network telephone, a so-called smartphone, which is customizable by application programs and which allows search for external information.

Depending on the thoughts, actions, and conditions of the user, the agent device 3 shows a reaction to the user U, i.e., "acts directly or indirectly," and the agent device 3 can: understand the intention of the user U to control the moving entity 2; and join a conversation through some sort of means such as by having a conversation through some sort of means such as utterance if there is only one person on board, the driver, or by providing a conversation topic in order to maintain amicable conversation among the occupants if there is more than one occupant including passenger(s). Thereby, the agent device 3 assists the occupants to experience a more comfortable ride.

The agent device 3 includes: a controller (or a control unit) 31, a storage unit 32, an output unit 33, a status recognition unit 34, a communication unit 35, and a processing unit 36.

The controller 31 includes a processor such as a CPU. The controller 31 has a processing result error detection program installed therein. The controller 31 is configured such that when the processing result error detection program is activated, the controller 31 functions as a behavior recognition unit 311, an emotion presumption (or feeling estimation) unit 312, a processing recognition unit 313, and a judgment (or determination) unit 314, which execute an arithmetic process to be described later. Moreover, of these, some or all may be implemented by hardware such as a large scale integration (LSI) or an application specific integrated circuit (ASIC), or may be implemented by a combination of software and hardware.

The controller 31 is configured such that the controller 31 can transmit and receive information to and from each of the storage unit 32, the output unit 33, the status recognition unit 34, the communication unit 35, and the processing unit 36.

The storage unit 32 is a storage device such as a RAM, a ROM (EEPROM), an HDD, or a removable card-type memory, and is configured to record various types of information. The storage unit 32 is configured such that the storage unit 32 can store and read user behavior information 321, executed processing information 322, user emotion information 323, error information 324, and feedback information 325, which are stored or used when the controller 31 executes the arithmetic process.

The output unit 33 includes an image display unit 331 and a voice (or audio) output unit 332.

The image display unit 331 is a display device such as a liquid crystal panel or a display which is capable of displaying images. The image display unit 331 displays a functional image or a navigation image in accordance with the functions of the program (processing result error detection program) installed in the controller 31.

The voice output unit 332 is a speaker, for example, and is configured to output voice in response to a signal inputted from the controller 31. In addition, the voice output unit 332 is configured to output to the controller 31 a signal indicating an operating status including e.g. voice being outputted.

The status recognition unit 34 includes an operation input unit 341, an image capturing unit 342, and a voice input unit 343.

The operation input unit 341 is an input device such as a touchpad which detects a touch operation by the user U. When the operation input unit 341 detects a touch operation, a signal representing the touch operation is outputted to the controller 31. The touch panel may be a combination of the operation input unit 341 and the image display unit 331. In addition to the above or alternatively, the operation input unit 341 may be an input device which is capable of detecting an operation by the user U such as a button, a keyboard, or a mouse.

The image capturing unit 342 is a camera, for example, and is configured to take a photo of the interior of the moving entity 2, convert the captured image to a signal, and to output the signal to the controller 31.

The voice input unit 343 is a microphone, for example, and is configured to detect the voice of the user U and to output to the controller 31 the detected voice in the form of a signal. The voice input unit 343 may be configured such that the controller 31 removes, from the signal, background noise such as voice being outputted from the voice output unit 332 and operating noise of the moving entity 2, allowing recognition of the voice of the user U.

The communication unit 35 includes a short-range communication unit 351 and a radio communication network communication unit 352.

The short-range communication unit 351 is configured to communicate interactively with the moving entity 2 or devices mounted on the moving entity 2 (for example, the sensor unit 21) via e.g. a wireless LAN inside the moving entity 2 in accordance with communication standards suitable for short-range radio communication or cabled communication involving, for example, a Universal Serial Bus (USB) connection cord, or Bluetooth (registered trademark).

The radio communication network communication unit 352 is configured to communicate interactively with external terminals such as the server 1 via the radio communication network in accordance with communication standards suitable for long-range radio communication involving e.g. WiFi™ which conforms to 3G, 4G, Long-Term Evolution (LTE), or IEEE802.X (X is replaced by b, c, ac, n etc.) standards.

The processing unit 36 includes a search unit 361 and a navigation unit 362.

The search unit 361 is configured such that by communicating with the server 1 via, for example, the radio communication network communication unit 352, the search unit 361 searches for information relevant to the designated keyword and outputs the results on the output unit 33.

The navigation unit 362 is configured such that by communicating with the server 1 via, for example, the radio communication network communication unit 352, the navigation unit 362 finds a route to the designated destination and outputs the results on the output unit 33.

The processing unit 36 may be configured such that by communicating with the moving entity 2 via the short-range communication unit 351, the processing unit 36 controls the operating status of each of the devices such as air conditioning equipment mounted on the moving entity 2.

At least one of the computers constituting the agent device 3 may include a computer outside the moving entity 2, for example, a constituent of the server 1. For instance, the server 1 may be configured to handle a request form the agent device 3 and then to make a response to the agent device 3, thereby functioning partly or totally as the controller 31 or the processing unit 36 of the agent device 3. Moreover, the server 1 may be configured to store or read data in response to a request from the agent device 3, thereby functioning partly or totally as the storage unit 32 of the agent device 3.

(Processing Result Error Detection Process)

With reference to FIGS. 3 to 7D, description is provided for the processing result error detection process executed by the controller 31.

Figure 3:
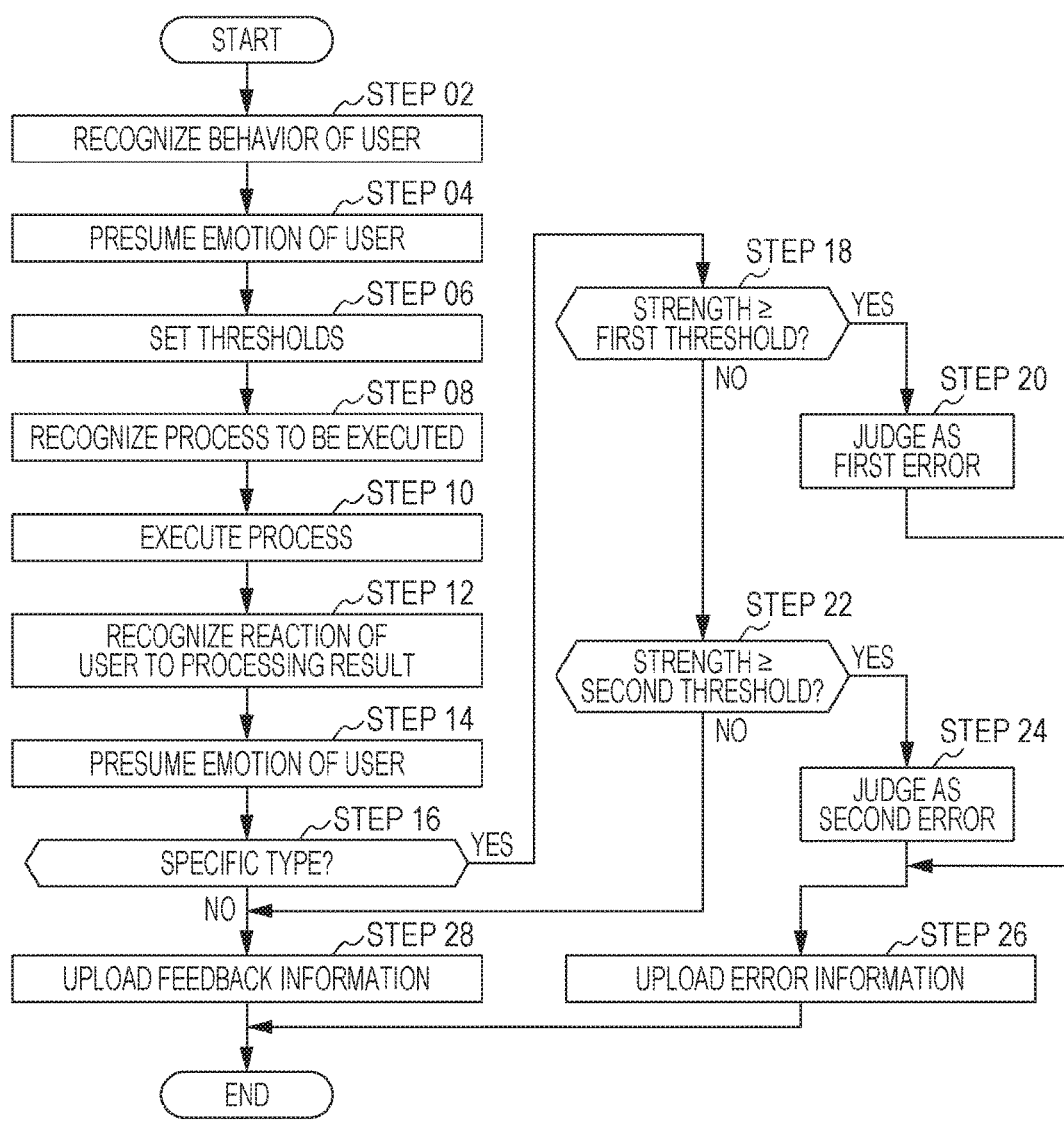
FIG. 3 is a flowchart of a processing result error detection process.

The behavior recognition unit 311 recognizes the behavior of the user U via the status recognition unit 34 (FIG. 3/STEP02). The behavior of the user U may be, for example, an operation by the user U detected by the operation input unit 341, the action or the facial expression of the user U captured by the image capturing unit 342, or the utterance by the user U detected by the voice input unit 343. The behavior recognition unit 311 adds and stores in the user behavior information 321 of the storage unit 32 the recognized behavior of the user U and the time of recognition of the behavior measured by a not-illustrated timer or a timer 371.

Figure 4:
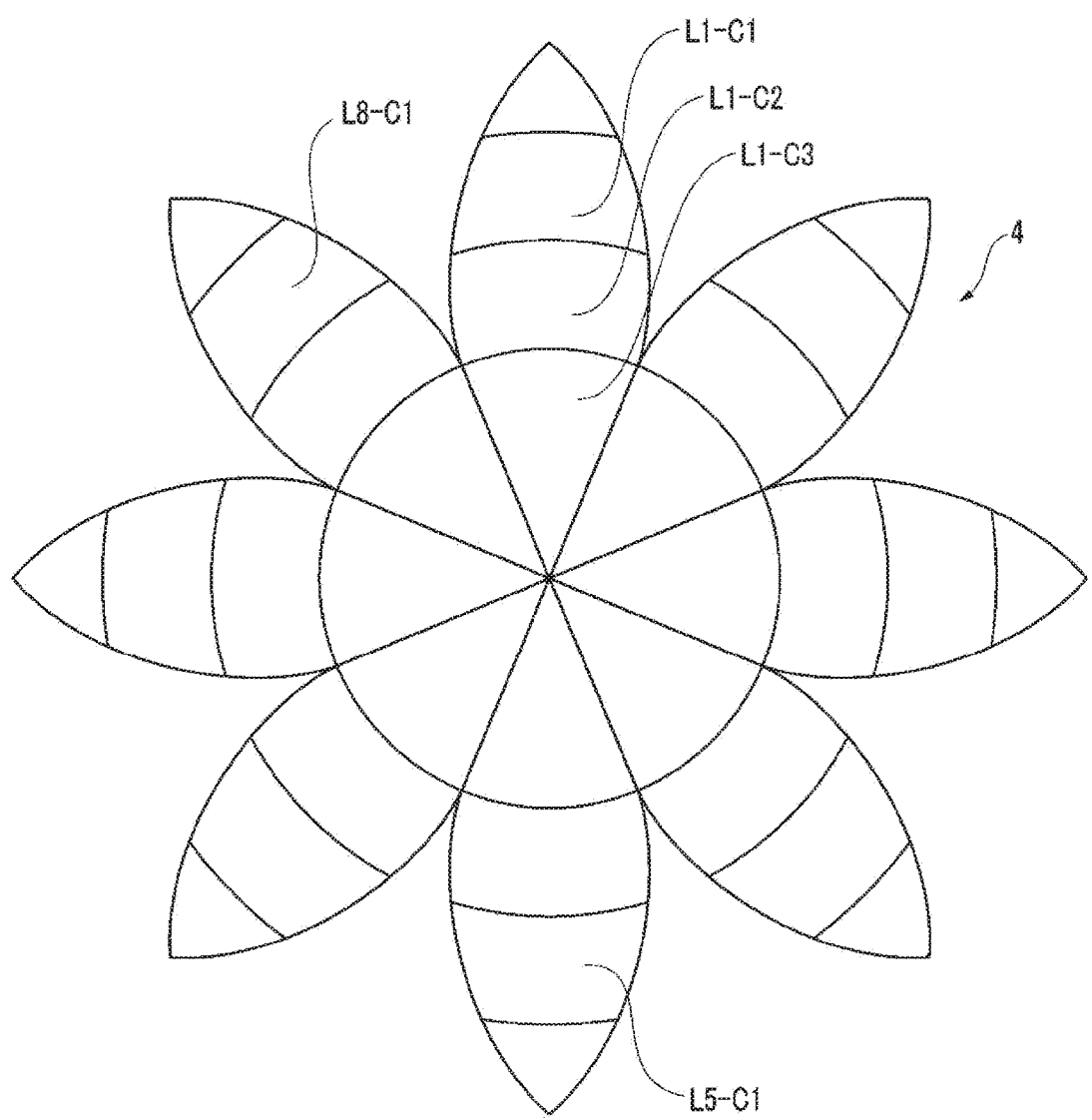
FIG. 4 is an explanatory diagram of a table presenting types of emotions.

The emotion presumption unit 312 presumes the emotion (or feeling) of the user U based on the behavior of the user U recognized at FIG. 3/STEP02 (FIG. 3/STEP04). For example, the emotion presumption unit 312 presumes the emotion of the user U by using a filter created through e.g. deep learning or a support vector machine, with the behavior of the user U as an input. The emotions of the user U are represented with an emotion table (or emotion model) as illustrated in FIG. 4. Emotions in deeper colors indicate more intense emotions of the user U. The emotion presumption unit 312 adds and stores in the user emotion information 323 of the storage unit 32 the presumed emotion of the user and the presumption date and time measured by a timer.

The emotions of the user U are represented according to the types of emotions and the intensity of emotion. In a proposition such as one by Plutchik, emotions are understood by classifying them into several types. For example, emotions include positive types of emotions such as liking, calmness, pleasantness, happiness, joy, trust, and anticipation, and negative types of emotions such as anxiety, dislike, pain, anger, and disgust. A known or novel emotion model presumes emotions. FIG. 4 illustrates a simplified version of the known emotion model by Plutchik. In the known emotion model by Plutchik, emotions are classified into four pairs of emotions, eight types in total: "joy, sadness, anger, fear, disgust, trust, surprise, and anticipation." The emotions are classified in the radial eight directions L1 . . . L5 to L8. The nearer the center of circle (C1 to C3), the more intense the emotions are. For example, joy L1 is classified into joy weak L1-C1, joy medium L1-C2, and joy intense L1-C3. The intensity of emotion is represented by a numerical value greater than or equal to 0, and may be interpreted such that the more intense an emotion, the stronger that emotion. The emotion of the user U is represented for each type by the intensity of each of the emotions assigned to the respective types.

The judgment unit 314 sets thresholds based on the emotion of the user U presumed at FIG. 3/STEP04 (FIG. 3/STEP06). For each type of emotion, the judgment unit 314 sets a first threshold and a second threshold which is smaller than the first threshold based on the presumed emotion of the user U. Details of the setting process for the thresholds are described later.

The processing recognition unit 313 determines and recognizes the process to be executed based on the behavior of the user U recognized at FIG. 3/STEP02 (FIG. 3/STEP08).

Here, consider the case of searching for "nearby shops serving SHIO RAMEN" while travelling in a vehicle. In this case, the user U pronounces "SHIO RAMEN." At FIG. 3/STEP08, the act of pronunciation by the user U is recognized as behavior of the user U.

The processing recognition unit 313 executes the process recognized at FIG. 3/STEP08 via the processing unit 36 (FIG. 3/STEP10). As a result, for example, a processing result at the processing unit 36 is outputted from the output unit 33, or the operating status of the instruments equipped on the moving entity 2 can be controlled. The processing recognition unit 313 adds the date and time of execution displayed by the timer and the processing result to the executed processing information 322 of the storage unit 32.

The behavior recognition unit 311 recognizes via the status recognition unit 34 the reaction (behavior) of the user U to the processing result at FIG. 3/STEP10 (FIG. 3/STEP12). The behavior recognition unit 311 adds and stores in the user behavior information 321 of the storage unit 32 the recognized behavior of the user U and the time of recognition of the behavior measured by the timer.

The emotion presumption unit 312 presumes the emotion of the user U based on the reaction of the user U recognized at FIG. 3/STEP12 (FIG. 3/STEP14). The emotion presumption unit 312 adds the presumed emotion of the user U and the presumption date and time displayed by the timer to the user emotion information 323 of the storage unit 32.

The judgment unit 314 judges whether or not the type of emotion of the user U is a specific type (FIG. 3/STEP16). The specific type here is, for example, dislike, anger, irritation, disappointment, happiness, liking, cheerfulness, and joy. If the user U has more than one type of emotion and the specific type is included in those types, the judgment unit 314 judges the judgment result at FIG. 3/STEP16 as positive.

FIG. 3/STEP16 is one of the processes for judging whether or not the processing result is erroneous. Here, the specific type includes not only negative types of emotions such as dislike, anger, irritation, and disappointment, but also positive types of emotions such as happiness, liking, cheerfulness, and joy because of the following reasons.

Figure 5:
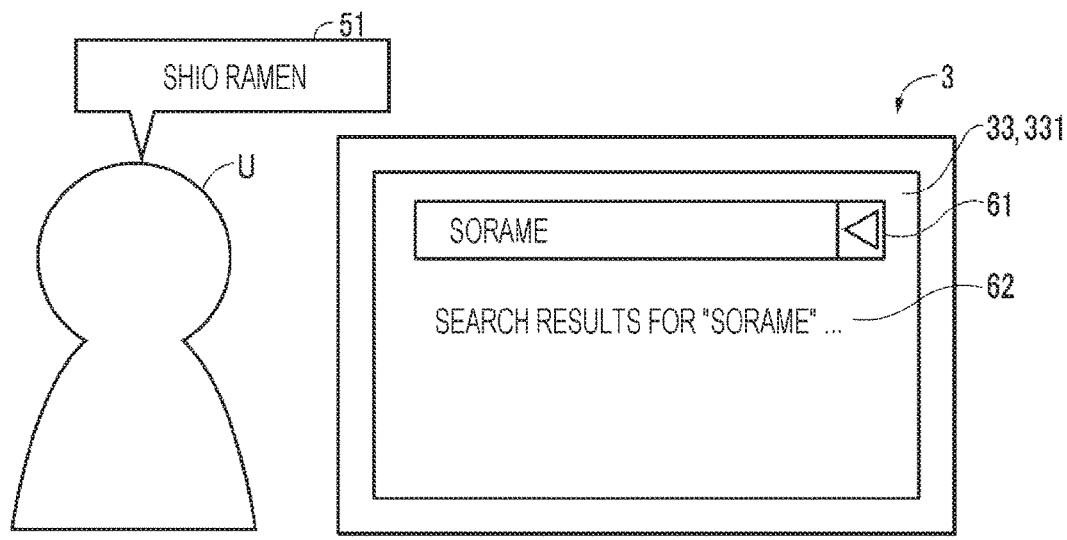
FIG. 5 is a diagram explaining an example of a recognition error.

As illustrated in FIG. 5, this is because the user U could express a positive emotion such as happiness, liking, and cheerfulness rather than a negative emotion such as dislike, anger, irritation, and disappointment due to e.g. funny unexpectedness of a search result 62 when the processing result is different from what the user expected, for example when the output unit 33 (image display unit 331) of the agent device 3 displays the search result 62 which is information relevant to "SORAME" 61 being a word irrelevant to "SHIO RAMEN" in spite of a remark 51, "SHIO RAMEN", by the user U.

If the judgment result at FIG. 3/STEP16 is affirmative (FIG. 3/STEP16: YES), the judgment unit 314 judges whether or not the intensity of emotion of the specific type of the user U is greater than or equal to the first threshold determined for that specific type (FIG. 3/STEP18).

If the judgment result is affirmative (FIG. 3/STEP18: YES), the judgment unit 314 judges the processing result as a first error with a recognition error of the behavior of the user U (FIG. 3/STEP20). The judgment unit 314 adds the behavior of the user U recognized at FIG. 3/STEP02, the processing result at FIG. 3/STEP10, and the first error to the error information 324 of the storage unit 32.

If the judgment result is negative (FIG. 3/STEP18: NO), the judgment unit 314 judges whether or not the intensity of emotion of the specific type of the user U is greater than or equal to the second threshold determined for that specific type (FIG. 3/STEP22).

If the judgment result is affirmative (FIG. 3/STEP22: YES), the judgment unit 314 judges the processing result as a second error without a recognition error of the behavior of the user U (FIG. 3/STEP24). The judgment unit 314 adds the behavior of the user U recognized at FIG. 3/STEP02, the processing result at FIG. 3/STEP10, and the second error to the error information 324 of the storage unit 32.

After the process at FIG. 3/STEP20 or FIG. 3/STEP24, the judgment unit 314 uploads the error information 324 to the server 1 (FIG. 3/STEP26).

If the judgment result of any of FIG. 3/STEP16 and FIG. 3/STEP22 is negative (FIG. 3/STEP16: NO or FIG. 3/STEP22: NO), the judgment unit 314 uploads the behavior of the user U recognized at FIG. 3/STEP02, the processing result at FIG. 3/STEP10, and feedback information indicating that no error is present to the server 1 (FIG. 3/STEP28).

Hereinafter, with reference to FIGS. 5 to 7A, the meanings of the processes at FIG. 3/STEP18 to FIG. 3/STEP24 will be supplemented.

In this specification, erroneous processing results are divided into the first error and the second error.

As illustrated in FIG. 5, the first error is an error resulting from an erroneous recognition of the behavior of the user such as the search result 62 for "SORAME" 61, which has a meaning and an initial sound both different from those of "SHIO RAMEN" in spite of the remark 51, "SHIO RAMEN", by the user U. In addition to the above, the first error includes, for example: a recognition error where the search word "SHIO RAMEN" is interpreted as "SHIORAHOMEN," which has the same initial sounds as "SHIO RAMEN", but has an absolutely different meaning; and a recognition error where a phrase with a different meaning is produced when the search sentence "search for nearby shops serving Hakata ramen or shio ramen" is erroneously interpreted to "shops in the Hakata district far from here" or "salt of Hakata", resulting from wrong recognition of the relationships between the words.

Figure 6:
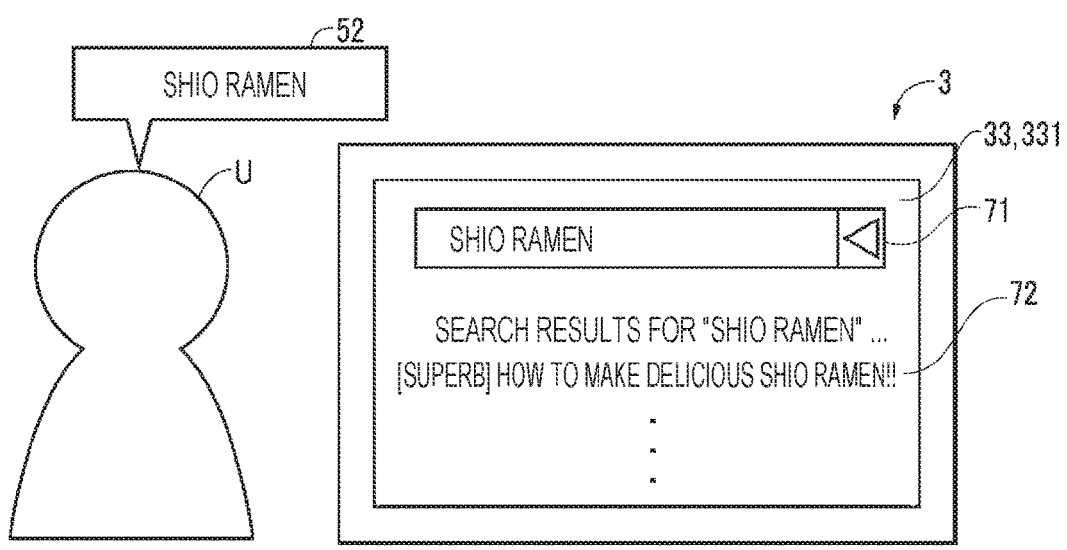
FIG. 6 is a diagram explaining another example of the recognition error.

As illustrated in FIG. 6, the second error is an error without an erroneous recognition of the behavior of the user U such as when a search result 72 for the keyword "SHIO RAMEN" 71 corresponding to the remark "SHIO RAMEN" 52 by the user U is different from what the user U expected because the user U expected search results for shops serving "SHIO RAMEN." In addition to the above, the second error includes, for example: a recognition error where, due to failure to recognize part of the pronounced search keyword "SHIO RAMEN," only the remaining part (for example, the latter part) "ramen" is recognized; and a recognition error where, for the search sentence "search for nearby shops serving Hakata ramen or shio ramen," although each of the words is properly recognized, the search results are not what the user expected, for example where stores selling foodstuff or family restaurant menus are presented.

In the above errors, since the first error tends to produce more unexpected result to user U compared to the second error, the first error tends to stir a more intense emotion in the user U compared to the second error. For example, in the case of the first error illustrated in FIG. 5, the user U could laugh out loud or say the result is different from his/her expectation, finding the result "impossible." In addition, in the case of the second error illustrated in FIG. 6, the user U could be disappointed saying "a place to eat" or "I was expecting a specialty shop," or say "the result is different from my expectation."

Figure 7A:
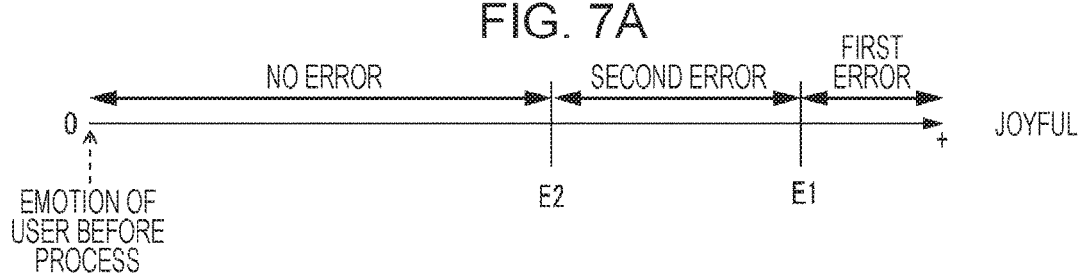
FIG. 7A is a diagram illustrating an example of setting thresholds for a positive emotion.

Thus, as illustrated in FIG. 7A, if, for example, the intensity of happiness emotion of the user U is equal to or greater than a happiness first threshold E1 (FIG. 3/STEP18: YES), the judgment unit 314 judges the processing result as the first error. On the other hand, if, for example, the intensity of happiness emotion of the user U is less than the happiness first threshold E1 (FIG. 3/STEP18: NO) and equal to or greater than a second threshold E2 (FIG. 3/STEP22: YES) which is smaller than the first threshold E1, the judgment unit 314 judges the processing result as the second error.

In such a manner, it is possible to distinguish the first error and the second error and detect a difference between them.

Description is provided for the setting of the thresholds at FIG. 3/STEP06, which has not been explained until now.

Figure 7B:
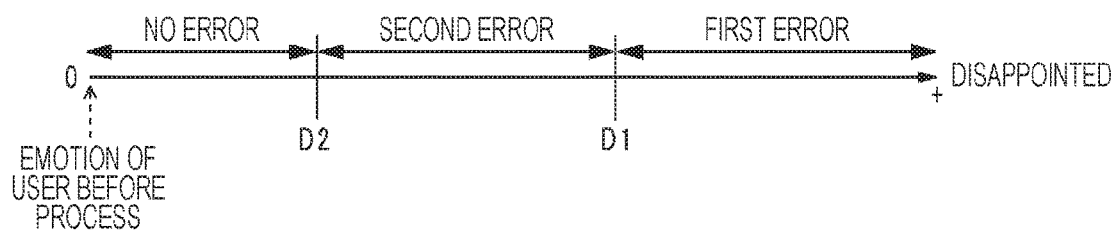
FIG. 7B is a diagram illustrating an example of setting thresholds for a negative emotion.

As illustrated in FIGS. 7A and 7B, it is desirable for the judgment unit 314 to set smaller the thresholds D1, D2 representing negative types of emotions such as disappointment compared to the thresholds E1, E2 representing positive types of emotions such as happiness. This is because it is possible to mitigate or eliminate negative types of emotions of the user U by recognizing as erroneous a processing result which causes negative types of emotions, and recovering from an error or taking a measure to prevent an error.

Also, it is preferable for the judgment unit 314 to set the thresholds based on the emotion of the user U presumed at FIG. 3/STEP04.

Figure 7C:
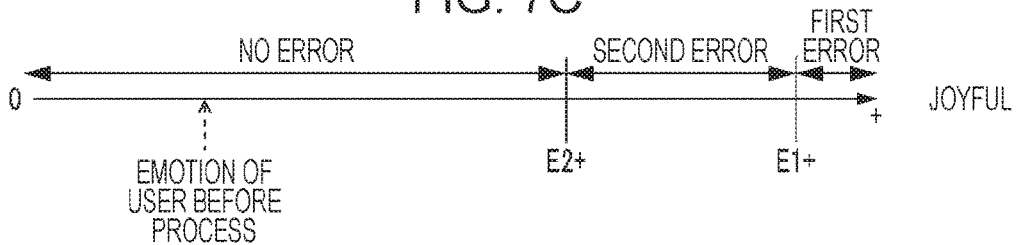
FIG. 7C is a diagram illustrating an example of setting thresholds for a positive emotion when an emotion of a user is presumed to be a positive emotion.
Figure 7D:
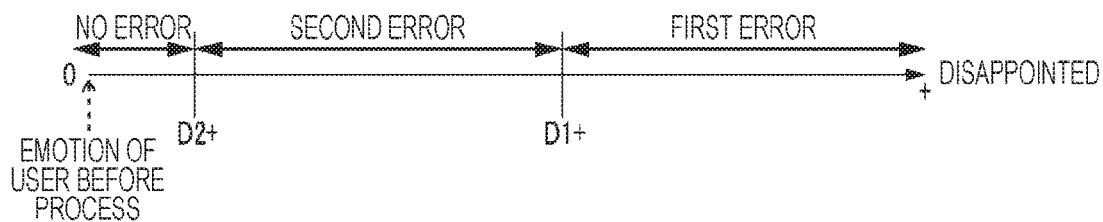
FIG. 7D is a diagram illustrating an example of setting thresholds for a negative emotion when the emotion of the user is presumed to be a negative emotion.

For example, with regard to the emotion of the user U presumed at FIG. 3/STEP04, if the intensity of positive types of emotions such as happiness is equal to or greater than a predetermined value, it is preferable that thresholds E1+, E2+ for positive types of emotions be set greater than the thresholds E1, E2 in the case where the emotion of the user U is normal (where the intensity of the emotion is zero) as illustrated in FIG. 7C, and that thresholds D1+, D2+ for negative types of emotions be set less than the thresholds D1, D2 in the case where the emotion of the user U is normal as illustrated in FIG. 7D. Additionally, with regard to the emotion of the user U presumed at FIG. 3/STEP04, if the intensity of negative types of emotions such as disappointment is equal to or greater than a predetermined value, it is preferable that the thresholds for negative types of emotions be set greater than the thresholds in the case where the emotion of the user U is normal, and that the thresholds for positive types of emotions be set less than the thresholds in the case where the emotion of the user U is normal. In such a manner, it is possible to perform error judgment by considering the emotion of the user U before the process.

Operation and Effect of Embodiment

According to the agent device 3, the processing result error detection program, the processing result error detection method, and the moving entity 2 of this configuration, the intensity of emotion of the user U is presumed based on the reaction of the user U to the processing result (FIG. 3/STEP14), and if the intensity of emotion of the user is equal to or greater than a predetermined threshold (FIG. 3/STEP18: YES or FIG. 3/STEP22: YES), the processing result is judged as erroneous (FIG. 3/STEP20 or FIG. 3/STEP24).

Here, the case where the intensity of emotion of the user U is equal to or greater than a predetermined threshold means the case where the processing result is one unexpected to the user U as illustrated in FIG. 5 or FIG. 6, and in addition, it is highly possible that the result be different from what the user U expected, i.e. the result be an erroneous processing result.

Since the processing result is judged based on the reaction of the user U to the processing result (FIG. 3/STEP18 or FIG. 3/STEP22), it is unnecessary for the user U to, for example, input whether or not the processing result is as expected. This reduces or eliminates bother given to the user U.

Thus, according to the agent device 3, the processing result error detection program, the processing result error detection method, and the moving entity 2 of the present disclosure, it is possible to accurately detect an erroneous processing result while reducing or solving bother given to the user U.

Further, according to the agent device 3, the processing result error detection program, the processing result error detection method, and the moving entity 2 of the above-described configuration, if the type of emotion of the user U is a negative one, smaller values are set as thresholds compared to the case where the type of emotion of the user U is a positive one (FIG. 3/STEP06, FIGS. 7A to 7D).

Hence, it is highly possible that the result be judged as erroneous if a negative emotion is expressed. Negative types of emotions expressed by the user U can be mitigated or eliminated by executing an additional process based on such an erroneous judgment result or by learning how to reduce potential erroneous processes.

In the case of a processing result with an erroneous recognition of the user U (FIG. 5), it is presumed that the intensity of the user be stronger compared to the case of a processing result without an erroneous recognition of the user U (FIG. 6).

According to the agent device 3, the processing result error detection program, the processing result error detection method, and the moving entity 2 of this configuration, which are configured in view of the foregoing, the reaction of the user U makes it possible to accurately recognize the type of erroneous processing result.

Even when the processing result is erroneous, the reaction of the user U can be different depending on the emotion of the user U before the process. In the agent device 3, the processing result error detection program, the processing result error detection method, and the moving entity 2 which are configured in view of this, since the thresholds are determined based on the emotion of the user U before the process (FIG. 3/STEP06, FIGS. 7B to 7D), a judgment is made as to whether or not the processing result is erroneous in consideration of the emotion of the user U before the process.

If the processing result is different from what the user U expected, the type of emotion expressed by the user U is limited. According to the agent device 3, the processing result error detection program, the processing result error detection method, and the moving entity 2 of this configuration, if the type of emotion of the user U is a specific type of emotion (FIG. 3/STEP16: YES), the processing result is judged as erroneous (FIG. 3/STEP20 or FIG. 3/STEP24). This improves the accuracy of detecting an erroneous processing result.

Even when the processing result is different from what the user U expected, the user U could express a positive emotion when, for example, the user U feels funny about an unexpected result. In the agent device 3, the processing result error detection program, the processing result error detection method, and the moving entity 2 of this configuration, since the processing result is judged as erroneous (FIG. 3/STEP20 or FIG. 3/STEP24) if the intensity of emotion is equal to or greater than a threshold (FIG. 3/STEP18: YES, FIG. 3/STEP22: YES, FIGS. 7A to 7D) even when the user U expresses a positive emotion, it is possible to improve the accuracy of detecting an erroneous processing result.

Modified Embodiments

The embodiment uses the first threshold and the second threshold. Instead, one of these thresholds may be used to detect only the first error or both of the first error and the second error without distinguishment.

The embodiment uploads error information at FIG. 3/STEP26. In addition to the above or alternatively, the controller 31 may execute a process of recovering from an erroneous state by, for example, performing recognition again after changing the recognition method if the processing result is the first error, or by executing the process again after changing the processing content from e.g. a search process to e.g. navigation if the processing result is the second error.

Additionally, since the first error might be because of failure of recognition due to the user speaking too fast, the controller 31 may calm down the user by playing voice asking the user to speak more slowly, or by performing control of playing music.

In the embodiment, the judgment unit 314 judges whether or not the type of emotion is the specific type (FIG. 3/STEP16). This process may be omitted to perform the process at FIG. 3/STEP18.

In the embodiment, the behavior recognition unit 311 recognizes the behavior of the user U based on the input from the status recognition unit 34 provided in the agent device 3. In addition to the above or alternatively, the behavior of the user U may be recognized by communicating with a mobile terminal carried by the user U.

Alternatively or in addition to the configuration where the processing unit 36 outputs the processing result to the output unit 33 provided in the agent device 3, the processing result may be outputted to an output unit of the mobile terminal carried by the user U. Although a specific form of embodiment has been described above and illustrated in the accompanying drawings in order to be more clearly understood, the above description is made by way of example and not as limiting the scope of the invention defined by the accompanying claims. The scope of the invention is to be determined by the accompanying claims. Various modifications apparent to one of ordinary skill in the art could be made without departing from the scope of the invention. The accompanying claims cover such modifications.

We claim:

1. A processing result error detection device comprising:
  a processor configured to implement controllers comprising:
    a behavior recognition controller configured to recognize behavior of a user including reaction of the user;
    a processing controller configured to execute a process dependent on the behavior of the user;
    an emotion presumption controller configured to presume an intensity of first emotion of the user, before the process being executed, based on behavior of the user corresponding to an instruction of the user, and presume an intensity of second emotion of the user by using reaction of the user to a processing result of the process executed by the processing controller; and
    a judgment controller configured to adjust a predetermined threshold by using the intensity of the first emotion of the user before the process being executed and judge that the processing result includes an error when the presumed intensity of the second emotion of the user is equal to or greater than the predetermined threshold.

2. The processing result error detection device according to claim 1, wherein
  the emotion presumption controller is configured to presume a type of emotion of the user as well as the intensity of emotion of the user by using the reaction of the user to the processing result, and
  in a case where the type of emotion of the user is a negative emotion type, the judgment controller sets the threshold to a smaller value than in a case where the type of emotion of the user is a positive emotion type.

3. The processing result error detection device according to claim 1, wherein
  the judgment controller judges that the processing result includes a first error with erroneous recognition of an instruction of the user when the intensity of emotion of the user is equal to or greater than a predetermined first threshold, and judges the processing result includes a second error without the erroneous recognition of the instruction of the user when the intensity of emotion of the user is less than the first threshold and is equal to or greater than a second threshold, the second threshold being smaller than the first threshold.

4. The processing result error detection device according to claim 1, wherein
  the emotion presumption controller is configured to presume a type of emotion of the user as well as the intensity of emotion of the user by using the reaction of the user in response to the processing result, and
  the judgment controller judges that the processing result includes the error when the type of emotion of the user is a specific type and the intensity of emotion of the user is equal to or greater than the threshold.

5. The processing result error detection device according to claim 4, wherein
  the specific type includes a positive type of emotion.

6. A moving entity comprising the processing result error detection device according to claim 1.

7. The processing result error detection device according to claim 1, wherein, when the intensity of emotion of the user before the process being executed is equal to or larger than a predetermined value and the emotion is positive type of emotion, the judgment controller adjusts the threshold to be larger value for positive type of emotion and adjusts the threshold to be smaller value for negative type of emotion.

8. The processing result error detection device according to claim 1, wherein, when the intensity of emotion of the user before the process being executed is equal to or larger than a predetermined value and the emotion is negative type of emotion, the judgment controller adjusts the threshold to be larger value for negative type of emotion and adjusts the threshold to be smaller value for positive type of emotion.

9. The processing result error detection device according to claim 1, wherein the processing result error detection device is equipped to a vehicle, the user is a passenger of the vehicle, and the processing controller outputs the processing result by using a display or a speaker to the passenger.

10. A non-transitory computer readable medium storing a processing result error detection program which causes a computer to execute processing comprising steps of:
    recognizing behavior of a user including reaction of the user;
    presuming an intensity of first emotion of the user, before the process being executed, based on behavior of the user corresponding to an instruction of the user;
    adjusting a predetermined threshold by using the intensity of the first emotion of the user before the process being executed;
    executing a process dependent on the behavior of the user;
    presuming an intensity of second emotion of the user by using the reaction of the user to a processing result of the process executed; and
    judging that the processing result includes an error when the presumed intensity of the second emotion of the user is equal to or greater than the predetermined threshold.

11. A processing result error detection method which is executed by a computer, the method comprising steps of:
    recognizing behavior of a user including reaction of the user;
    presuming an intensity of first emotion of the user, before the process being executed, based on behavior of the user corresponding to an instruction of the user;
    adjusting a predetermined threshold by using the intensity of the first emotion of the user before the process being executed;
    executing a process dependent on the behavior of the user;
    presuming an intensity of second emotion of the user by using the reaction of the user to a processing result of the process executed; and
    judging that the processing result includes an error when the presumed intensity of the second emotion of the user is equal to or greater than the predetermined threshold.

\* \* \* \* \*